United States Patent
Franzke et al.

(10) Patent No.: US 10,421,711 B2
(45) Date of Patent: Sep. 24, 2019

(54) PROCESS FOR MAKING A CRYSTALLINE ALKALI METAL SALT OF A COMPLEXING AGENT, AND CRYSTALLINE COMPLEXING AGENT

(71) Applicant: BASF SE, Ludwigshafen am Rhein (DE)

(72) Inventors: Constanze Franzke, Duesseldorf (DE); Axel Franzke, Duesseldorf (DE); Armin Stamm, Nieder-Olm (DE); Markus Hartmann, Neustadt (DE); Robert Baumann, Mannheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/061,007

(22) PCT Filed: Dec. 7, 2016

(86) PCT No.: PCT/EP2016/080001
§ 371 (c)(1),
(2) Date: Jun. 11, 2018

(87) PCT Pub. No.: WO2017/102483
PCT Pub. Date: Jun. 22, 2017

(65) Prior Publication Data
US 2018/0354891 A1    Dec. 13, 2018

(30) Foreign Application Priority Data
Dec. 17, 2015 (EP) .................................. 15200850

(51) Int. Cl.
| | | |
|---|---|---|
| *C07C 227/10* | (2006.01) | |
| *C07C 227/18* | (2006.01) | |
| *C07C 227/42* | (2006.01) | |
| *C07C 227/02* | (2006.01) | |
| *C07C 229/36* | (2006.01) | |
| *C11D 3/33* | (2006.01) | |

(52) U.S. Cl.
CPC .......... *C07C 229/36* (2013.01); *C07C 227/02* (2013.01); *C07C 227/10* (2013.01); *C07C 227/18* (2013.01); *C07C 227/42* (2013.01); *C11D 3/33* (2013.01)

(58) Field of Classification Search
CPC ... C07C 229/36; C07C 227/42; C07C 227/02; C07C 227/26; C07C 227/18; C07C 227/10; C11D 3/33
See application file for complete search history.

(56) References Cited

U.S. PATENT DOCUMENTS

| | | | |
|---|---|---|---|
| 5,786,313 A | 7/1998 | Schneider et al. | |
| 6,005,141 A | 12/1999 | Schneider et al. | |
| 6,008,176 A | 12/1999 | Schneider et al. | |
| 8,628,684 B2 * | 1/2014 | Mrzena ................. | C07C 227/42 252/182.3 |
| 9,227,915 B2 * | 1/2016 | Oftring ................. | C07C 227/42 |

FOREIGN PATENT DOCUMENTS

| | | | |
|---|---|---|---|
| DE | 19819187 A1 | 11/1999 | |
| EP | 0845456 A2 | 6/1998 | |
| EP | 0851023 A2 | 7/1998 | |
| EP | 0845456 B1 * | 6/2001 | ........... C07C 227/42 |
| WO | WO 94/29421 | 12/1994 | |
| WO | WO 2012/150155 A1 | 11/2012 | |

OTHER PUBLICATIONS

Rouhi, Chemical and Engineering News, The Right Stuff, 2003, 81(8), pp. 32-35. (Year: 2003).*
International Search Report dated Feb. 13, 2107, in PCT/EP2016/080001, filed Dec. 7, 2016.
Extended European Search Report dated Jun. 15, 2016 in European Patent Application No. 15200850.4, 3 pages.

* cited by examiner

*Primary Examiner* — Paul A Zucker
(74) *Attorney, Agent, or Firm* — Oblon, McClelland, Maier & Neustadt, L.L.P.

(57) ABSTRACT

Process for manufacturing a crystalline alkali metal salt of the general formula (I) $[R^1-CH(COO)-N(CH_2-COO)_2] M^1_3$ (I) wherein $M^1$ is selected from alkali metal cations, same or different, $R^1$ is selected from $C_1$-$C_4$-alkyl and $CH_2CH_2COOM^1$, comprising the step of (b) crystallizing said alkali metal salt from an aqueous solution containing in the range of from 5 to 30% by weight of alkali metal hydroxide, referring to said aqueous solution.

15 Claims, 2 Drawing Sheets

PROCESS FOR MAKING A CRYSTALLINE ALKALI METAL SALT OF A COMPLEXING AGENT, AND CRYSTALLINE COMPLEXING AGENT

CROSS-REFERENCE TO RELATED APPLICATIONS

The present application is a 35 U.S.C. § 371 national stage patent application of International patent application PCT/EP2016/080001, filed on Dec. 7, 2016, the text of which is incorporated by reference, and claims the benefit of the filing date of EP application no. 15200850.4, filed on Dec. 17, 2015, the text of which is also incorporated by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

STATEMENT REGARDING PRIOR DISCLOSURES BY THE INVENTOR OR A JOINT INVENTOR. Not Applicable.

BACKGROUND OF THE INVENTION

Field of the Invention

The present invention is directed towards a process for manufacturing a crystalline alkali metal salt of the general formula (I)

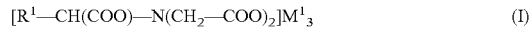  (I)

wherein
$M^1$ is selected from alkali metal cations, same or different, $R^1$ is selected from $C_1$-$C_4$-alkyl and $CH_2CH_2COOM^1$, comprising the step of
(b) crystallizing said alkali metal salt from an aqueous solution containing in the range of from 5 to 30% by weight of alkali metal hydroxide, referring to said aqueous solution.

Furthermore, the present invention is directed towards a crystalline alkali metal salt, and to its use.

Description of the Related Art Including Information Disclosed Under 37 CFR 1.97 and 1.98

Chelating agents of the aminocarboxylate type such as methyl glycine diacetic acid (MGDA) and glutamic acid diacetic acid (GLDA) and their respective alkali metal salts are useful sequestrants for alkaline earth metal ions such as $Ca^{2+}$ and $Mg^{2+}$. A lot of aminocarboxylates show good biodegradability and are thus environmentally friendly. For that reason, they are recommended and used for various purposes such as laundry detergents and for automatic dishwashing (ADW) formulations, in particular for so-called phosphate-free laundry detergents and phosphate-free ADW formulations.

A general problem of many aminocarboxylates is their hygroscopicity. In solid formulations such as granules or powders, said hygroscopicity may lead to a reduction or even a complete loss of flowability. Aminocarboxylates will then easily form a sticky mass. In tablets or other solid ready-to-use formulations, said hygroscopicity may lead to reactions of aminocarboxylate with other components of said formulation, or to reactions of other components among each other, for example of peroxide or percarbonate with enzyme. Such reactions are highly undesirable and may lead to a partial or complete deactivation of components of a solid formulation.

The problem of hygroscopicity has been addressed by various authors. In EP 0 845 456 A, an aqueous water-containing melt of MGDA is allowed to solidify. A crystalline mass is obtained. However, it is tedious to remove such mass from the crystallizing vessel, and the degree of crystallinity leaves room for improvement. In WO 2012/150155, comparably enantiomerically pure samples of L-MGDA-$Na_3$ were synthesized. The crystallization of such enantiomerically pure MGDA yields much better crystals but the synthesis is tedious.

It was therefore an objective of the present invention to provide environmentally friendly complexing agents that show a reduced hygroscopicity as judged from their crystallinity, and improved stability towards percarbonate. It was further an objective of the present invention to provide a process for making such complexing agents, and it was an objective to provide applications of such complexing agents.

BRIEF SUMMARY OF THE INVENTION

Accordingly, the process defined at the outset has been found, hereinafter also referred to as inventive process or as process according to the (present) invention. The inventive process is a process for manufacturing a crystalline alkali metal salt of the general formula (I)

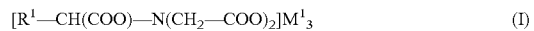  (I)

that is hereinafter also referred to as complexing agent according to formula (I)—wherein
$M^1$ is selected from alkali metal cations, same or different, for example lithium, sodium, potassium, rubidium, and cesium and from combinations of at least two of the foregoing, preferred are sodium and potassium and combinations of sodium and potassium. For example, $M^1_3$ may be selected from $Na_{3-x}K_x$ with x being in the range from 0.01 to 2.99, preferably $K_2Na$, $Na_2K$, $Na_{2.5}K_{0.5}$, $Na_{2.35}K_{0.65}$, $K_{2.5}Na_{0.5}$, and $K_{2.35}Na_{0.65}$. Even more preferred, in $M^1_3$ all $M^1$ are the same and either Na or K, Na being most preferred.

$R^1$ is selected from $C_1$-$C_4$-alkyl and $CH_2CH_2COOM^1$, preferred are methyl, ethyl, n-propyl, iso-propyl, n-butyl, iso-butyl, and sec.-butyl, preferred are iso-butyl and particularly preferred is methyl.

In $CH_2CH_2COOM^1$, $M^1$ is defined as above.

In a preferred embodiment of the present invention, $R^1$ is methyl and $M^1$ is sodium.

DETAILED DESCRIPTION OF THE INVENTION

Figure 1:
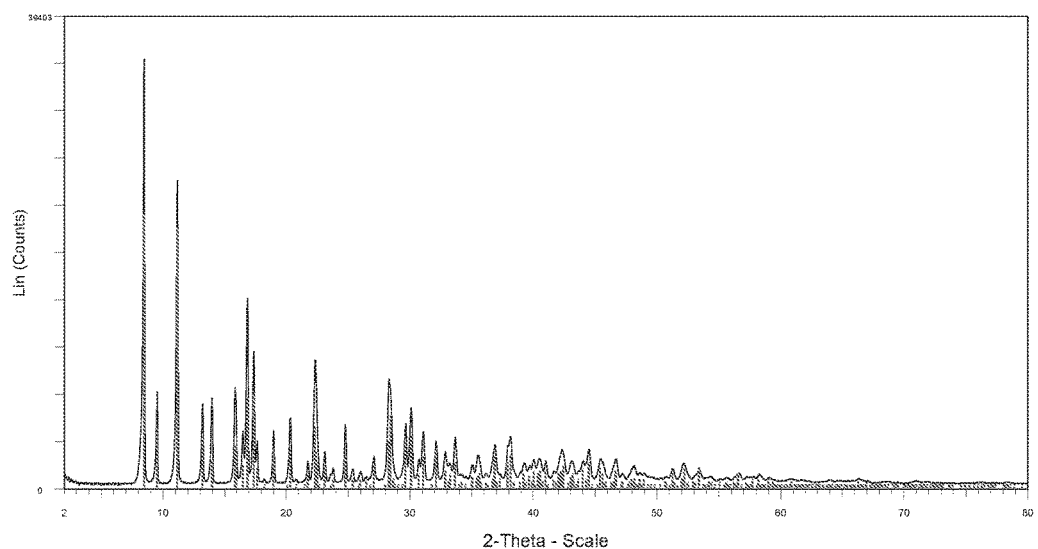
FIG. 1: An X-ray diffraction spectrum of inventive salt (S.1), which is the solid form of methyl glycine diacetic acid (MGDA) trisodium salt having a crystallinity of 98% as determined by X-ray diffraction.
Figure 2:
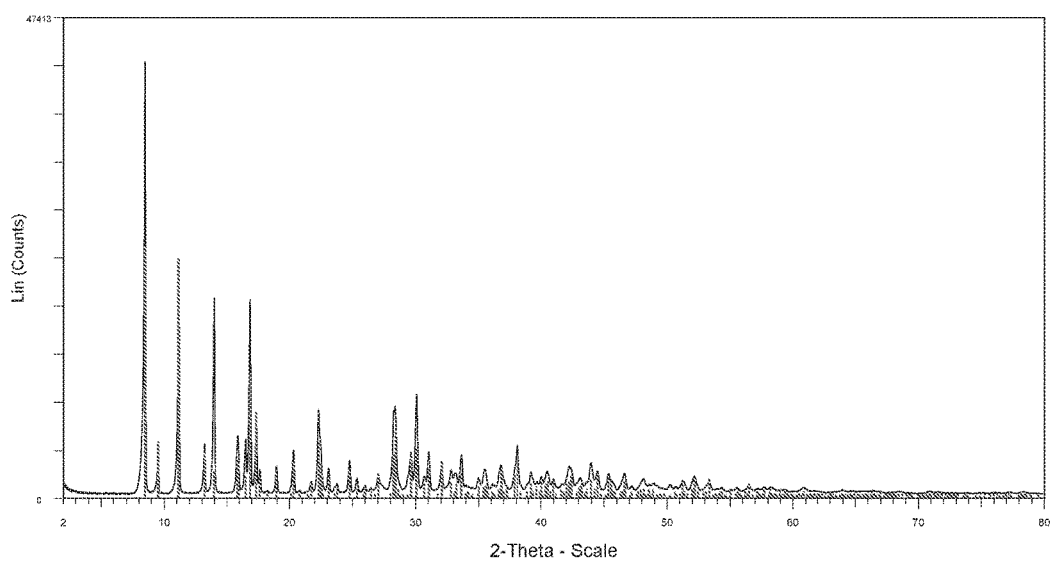
FIG. 2: An X-ray diffraction spectrum of inventive salt (S.2), which is the solid form of methyl glycine diacetic acid (MGDA) trisodium salt having a crystallinity of 98% as determined by X-ray diffraction.

Complexing agent according to formula (I) may be present as racemic mixture (D,L) or as pure L- or D-enantiomer—of which the L-enantiomer is preferred—or as mixture of L- and D-enantiomers in which one of the enantiomers is predominantly present, sometimes termed as scalemic mixtures, for example in mixtures with an enantiomeric excess (ee) of the L-enantiomer in the range of from 0.1 to 85%. Preferred are racemic mixtures and mixtures of enantiomers containing predominantly the respective L-isomer with an enantiomeric excess (ee) in the range of from 0.1 to 85%, even more preferred from 2.5% to 50%. Most preferred is the racemic mixture.

The enantiomeric excess can be determined by measuring the polarization (polarimetry) or preferably by chromatography, for example by HPLC with a chiral column, for example with one or more cyclodextrins as immobilized phase. Preferred is determination of the ee by HPLC with an immobilized optically active ammonium salt such as D-penicillamine.

The inventive process comprises the step of
(b) crystallizing said alkali metal salt from an aqueous solution containing in the range of from 5 to 30% by weight of alkali metal hydroxide, referring to said aqueous solution.

For that purpose, step (b) of the inventive process starts with a solution of complexing agent according to formula (I) in an aqueous solution containing in the range of from 5 to 30% by weight of alkali metal hydroxide, referring to said aqueous solution.

Said alkali metal hydroxide is selected from hydroxides of lithium, sodium, potassium, rubidium or cesium or combinations of at least two of the foregoing, for example combinations of sodium hydroxide and potassium hydroxide. Preferred are sodium hydroxide and potassium hydroxide. The alkali metal in alkali metal hydroxide corresponds to M in complexing agent according to formula (I).

Said solution may result directly from the synthesis of complexing agent according to formula (I), but other methods to provide such solutions are possible as well. Methods for providing such a solution are discussed further down below.

The inventive process refers to crystallizing such complexing agent according to formula (I) from an aqueous solution of alkali metal hydroxide. In the context of the present invention, crystallizing—or crystallization, both terms are hereinafter used interchangeably—is effected by making a supersaturated solution of the respective aminocarboxylate in aqueous alkali metal hydroxide solution and then allowing the respective aminocarboxylate to precipitate in the form of crystals.

Crystallization may be selected from evaporation crystallization, cooling crystallization, and vacuum cooling crystallization. Vacuum cooling crystallization refers to processes wherein the crystallization is performed under reduced pressure, for example 10 to 500 mbar, under preferably adiabatic removal of water. Preferred is cooling crystallization.

In the course of the inventive process it is usually avoided to produce a supersaturated melt or supersaturated water-containing melt. The aqueous solution from which complexing agent according to formula (I) is crystallized in the course of the present invention therefore has a contents of complexing agent according to formula (I) of 5 up to 60% by weight, preferably from 15 up to 45% by weight.

In one embodiment of the present invention step (b) comprises providing an aqueous solution of alkali metal salt of general formula (I) in an aqueous solution of alkali metal hydroxide, said solution having a temperature of at least 50° C., for example in the range of from 50 to 100° C., preferably from 75 to 90° C., and cooling down said solution to 35° C. or less at a cooling rate of 0.05 to 1.5 K/min, for example to a temperature in the range of from zero to 35° C.

In one embodiment of the present invention, step (b) comprises providing an aqueous solution of alkali metal salt of general formula (I) in an aqueous solution of alkali metal hydroxide, said solution having a temperature of at least 50° C., for example in the range of from 50 to 100° C., preferably from 75 to 90° C., and then evaporating water at least partially at a temperature in the range of from 50 up to 100° C. and at a pressure in the range of from 50 mbar to 10 bar.

Preferably, step (b) is performed at a pressure in the range of from 300 to 400 mbar.

In one embodiment of the present invention step (b) is performed under stirring. In other embodiments, step (b) is performed without stirring.

In one embodiment of the present invention, the aqueous solution from which alkali metal salt of general formula (I) is crystallized has a pH value in the range of from 10 to 14, preferably 13.5 to 14.

In one embodiment of the present invention, providing an aqueous solution of alkali metal salt of compound of general formula (I) is achieved as follows:

(a1) saponification of at least one nitrile according to general formula (II a) or (II b)

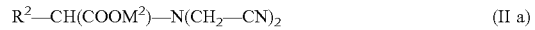

$$R^2\text{---}CH(COOM^2)\text{---}N(CH_2\text{---}CN)_2 \qquad (\text{II a})$$

$$R^2\text{---}CH(CN)\text{---}N(CH_2\text{---}CN)_2 \qquad (\text{II b})$$

wherein
$R^2$ is selected from $C_1$-$C_4$-alkyl, $CH_2CH_2COOH$ and $CH_2CH_2COOM^1$,
$M^1$ being defined as above, and
$M^2$ being selected from hydrogen and alkali metal,
with an excess of aqueous alkali metal hydroxide solution before subjecting the resultant aqueous solution to step (b).

In step (a1), the term "excess of aqueous alkali metal hydroxide solution" refers to a molar amount of alkali metal hydroxide that exceeds the sum of molar amounts of nitrile groups and COOH groups of compounds of formula (II a) or formula (II b), respectively.

In one embodiment of the present invention, providing an aqueous solution of alkali metal salt of compound of general formula (I) is achieved as follows:

(a2) saponification of at least one nitrile according to general formula (II a) or (II b)

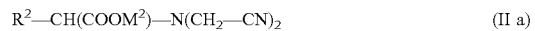

$$R^2\text{---}CH(COOM^2)\text{---}N(CH_2\text{---}CN)_2 \qquad (\text{II a})$$

$$R^2\text{---}CH(CN)\text{---}N(CH_2\text{---}CN)_2 \qquad (\text{II b})$$

wherein
$R^2$ is selected from $C_1$-$C_4$-alkyl, $CH_2CH_2COOH$ and $CH_2CH_2COOM^1$,
$M^2$ being selected from hydrogen and alkali metal,
with sub-stoichiometric or preferably with stoichiometric amounts of alkali metal hydroxide solution, (a3) adding aqueous alkali metal hydroxide solution before subjecting the resultant solution to step (b) or—preferably—adding aqueous alkali metal hydroxide solution during step (b).

In the context of the present invention, the term "stoichiometric amounts of alkali metal hydroxide solution" refers to a molar amount of alkali metal hydroxide that equals the sum of molar amounts of nitrile groups and carboxylate groups of compounds of formula (II a) or formula (II b), respectively.

The addition according to step (a3) may be performed in one step or in several sub-steps. Such addition may be performed within a few seconds or over some time, for example over 5 minutes up to 5 hours.

In a special embodiment of the present invention, providing an aqueous solution of alkali metal hydroxide may be achieved by (a1) saponification of at least one nitrile according to general formula (II a) or (II b)

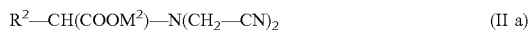  (II a)

  (II b)

wherein
$R^2$ is selected from $C_1$-$C_4$-alkyl, $CH_2CH_2COOH$ and $CH_2CH_2COOM^1$,
$M^1$ being defined as above, and
$M^2$ being selected from hydrogen and alkali metal,
with an excess of aqueous alkali metal hydroxide solution and then (a3) adding aqueous alkali metal hydroxide solution before subjecting the resultant solution to step (b) or adding aqueous alkali metal hydroxide solution during step (b).

In specific embodiments wherein step (b) is performed as vacuum cooling crystallization, it is possible to first distill off some water followed by addition of aqueous alkali metal hydroxide solution, or to add aqueous alkali metal hydroxide solution followed by removal of water, or to simultaneously remove water and add aqueous alkali metal hydroxide solution. It is preferred to first distill off some water followed by addition of aqueous alkali metal hydroxide solution.

In one embodiment of the present invention, a saponification of compound of formula (II a) or (II b) may be performed at a temperature in the range of from 25 to 200° C. The saponification of compound of formula (II a) or (II b) may be performed at constant temperature, or the temperature may be changed during the saponification reaction.

In one embodiment of the present invention, saponification of compound of formula (II a) or (II b) will be carried out in two steps at different temperatures, employing stoichiometric amounts of hydroxide or an excess of 1.01 to 1.5 moles of hydroxide per molar sum of COOH groups and nitrile groups of dinitrile of step (b), preferably 1.01 to 1.2 moles.

Different temperature means in the context of such saponifications that the respective saponification may be divided into sub-steps (a-α) and (a-β) and that the average temperature of step (a-α) is different from the average temperature of step (a-β). Preferably, step (a-α) is performed at a temperature lower than step (a-β). Even more preferably, step (a-β) is performed at an average temperature that is at least 100° C. higher than the average temperature of step (a-α).

Step (a-α) may be started by adding an aqueous solution containing compound of formula (II a) or (II b) to an aqueous solution of alkali metal hydroxide or adding an aqueous solution of alkali metal hydroxide to an aqueous solution containing compound of formula (II a) or (II b), the latter version being preferred. In another embodiment, an aqueous solution containing compound of formula (II a) or (II b) and an aqueous solution of alkali metal hydroxide are being added simultaneously to a vessel.

When calculating the stoichiometric amounts of hydroxide to be added in the saponification, the sum of COOH groups and nitrile groups from the total theoretical amount of compound of formula (II a) or (II b) is multiplied by 3 and the amounts of alkali already present from previous steps, if applicable, is subtracted.

Step (a-α) may be performed at a temperature in the range of from 20 to 80° C., preferable 40 to 70° C. In the context of step (a-α) "temperature" refers to the average temperature.

As a result of step (a-α), an aqueous solution of the respective diamide or triamide and its respective alkali metal salt may be obtained, M being alkali metal. Said solution may also contain L-MGDA and the corresponding monoamide and/or its mono- or dialkali metal salt.

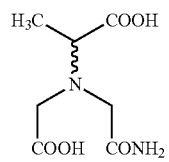

Step (a-β) may be performed at a temperature in the range of from 130 to 195° C., preferably 175 to 195° C. In the context of step (a-β) "temperature" refers to the average temperature.

In one embodiment of the present invention, step (a-β) has an average residence time in the range of from 5 to 180 minutes.

Depending on the type of reactor in which step (a-β) is being performed, such as an ideal plug flow reactor, the average residence time can be replaced by the residence time.

In one embodiment of the present invention, step (a-α) is carried out in a continuous stirred tank reactor and step (a-β) is carried out in a second continuous stirred tank reactor. In a preferred embodiment, step (a-α) is carried out in a continuous stirred tank reactor and step (a-β) is carried out in a plug flow reactor, such as a tubular reactor.

In one embodiment of the present invention, step (a-α) of the inventive process is carried out at elevated pressure, for example at 1.05 to 6 bar. In another embodiment, step (a-α) of the inventive process is carried at normal pressure.

Especially in embodiments wherein step (a-β) is carried out in a plug flow reactor, step (a-β) may be carried out at elevated pressure such as 1.5 to 40 bar, preferably at least 20 bar. The elevated pressure may be accomplished with the help of a pump or by autogenic pressure elevation.

Preferably, the pressure conditions of steps (a-α) and (a-β) are combined in the way that step (a-β) is carried out at a higher pressure than step (a-α).

In one embodiment of the present invention, the inventive process may comprise steps other than the steps disclosed above. Such additional steps may be, for example, one or more decolourization steps, for example with activated carbon or with peroxide such as $H_2O_2$.

In one embodiment of the present invention the aqueous solution that is subjected to step (b) of the invention is free from ammonia. Free from ammonia means a content of ammonia in the range of from 1 to 80 ppm of ammonia, preferably below 50 ppm. Such ammonia may be removed by stripping.

A further step that is preferably carried out after step (a) but before crystallization is stripping with nitrogen or steam in order to remove ammonia. Said stripping can be carried out at temperatures in the range of from 90 to 110° C. By nitrogen or air stripping, water can be removed from the solution so obtained. Stripping is preferably carried out at a pressure below normal pressure, such as 650 to 950 mbar.

The mother liquor obtained from the inventive process may be disposed of or completely or partially re-used, for example for saponification of fresh compound of formula (II a) or (II b).

After having obtained crystallized salts according to the inventive process such salts may be recovered according to conventional solid/liquid separation means, for example filtration, decanting, or with the help of a centrifuge, filtration being preferred. Filtration may be supported by exerting pressure or by applying reduced pressure. The crystals can be removed by solid/liquid separation with any solid/liquid separation apparatus, for example a suction filter, a rotary filter, a belt filter, a pusher centrifuge, a bowl centrifuge or the like, or without any specific apparatus. The removal may include a washing step and/or a drying step. Further suitable measure are washing with mother liquor, or with ice-cold water or preferably with an aqueous saturated MGDA trialkali metal salt solution, drying, especially under reduced pressure, for example 80 to 100° C. at 0.1 to 10 mbar, preferably 85 to 95° C. at 0.1 to 1 mbar, and even more preferably 90° C. at 0.1 mbar.

Crystallized salts obtained according to the inventive process show excellent properties, especially when used as sequestrant in cleaners for hard surfaces such as, but not limited to automatic dishwashing detergents, and in laundry detergents. Crystallized salts obtained according to the inventive process have low hygroscopicity and a low tendency to yellowing even in the presence of peroxides, percarbonates and/or perborates.

An further aspect of the present invention refers to a solid alkali metal salt of the general formula (I)

$$[R^1\text{—CH(COO)—N(CH}_2\text{—COO)}_2]M^1_3 \qquad (I)$$

hereinafter also referred to as inventive salts—wherein
$M^1$ is selected from alkali metal cations, same or different,
$R^1$ is selected from $C_1$-$C_4$-alkyl and $CH_2CH_2COOM^1$,
said solid alkali metal salt having a crystallinity in the range of from 90 to 99%, determined by X-ray diffraction.

$M^1$ is selected from alkali metal cations, same or different, for example lithium, sodium, potassium, rubidium, and cesium and from combinations of at least two of the foregoing, preferred are sodium and potassium and combinations of sodium and potassium. For example, $M^1_3$ may be selected from $Na_{3-x}K_x$ with x being in the range from 0.01 to 2.99, preferably $K_2Na$, $Na_2K$, $Na_{2.5}K_{0.5}$, $K_{2.5}Na_{0.5}$. even more preferred, in $M^1_3$ all $M^1$ are the same and either Na or K, Na being most preferred.

$R^1$ is selected from $C_1$-$C_4$-alkyl and $CH_2CH_2COOM^1$, preferred are methyl, ethyl, n-propyl, iso-propyl, n-butyl, iso-butyl, and sec.-butyl, preferred is iso-butyl and particularly preferred is methyl.

In $CH_2CH_2COOM^1$, $M^1$ is defined as above.

In a preferred embodiment of the present invention, $R^1$ is methyl and $M^1$ is sodium.

The degree of crystallinity, in the context of the present invention also simply referred to as crystallinity, was determined from the X-ray powder diffractograms in a known manner by, as usual, determining the surface fraction of the crystalline phase and of the amorphous phase and using these to calculate the degree of crystallinity, CD, as ratio of the area of the crystalline phase, $I_c$, to the total area, consisting of the combined areas of the amorphous phase, $I_a$, and the area of the crystalline phase, $I_c$:

$$CD=I_c/(I_c+I_a).$$

In particular, the determination of the degree of crystallinity can be carried out by using a software program, for example the software program TOPAS® from Bruker AXS.

The determination of the degree of crystallinity was performed using X-ray powder diffraction, according to the method of relative intensities. Data is collected on a standard Bragg-Brentano diffractometer, using CuKα radiation. The region of 2° to 50° (2θ) is scanned using a step size of 0.02°. A primary and secondary programmable motorized slit are set to ensure a constant illuminated sample length of 20 mm. The diffraction pattern is modelled using the Rietveld approach matching the calculated diffraction pattern to the experimental data. The following parameters enter into the model: linear background function, Lorentz- and polarization correction, the entire crystal structures of Form I and Form II of MGDA-Na₃. The latter contribute the crystalline intensity ($I_{crystalline}$) toward the modelled pattern. The amorphous intensity ($I_{amorphous}$) is modelled using two Lorentzian functions with centres at 8° (2θ) and 36.2° 2θ). The positions, intensities and peak widths were refined to match the measured data. This model was set up and refined in the commercial software TOPAS V4.2 (Bruker AXS GmbH, Karlsruhe). The crystallinity K was then determined using the function:

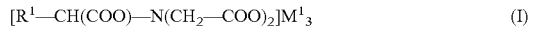

$$K = \frac{I_{crystalline}}{I_{crystalline} + I_{amorphous}}$$

In accordance with the explanations above, inventive salts may exist as racemic mixture (D,L) or as pure L- or D-enantiomer—of which the L-enantiomer is preferred—or as mixture of L- and D-enantiomers in which one of the enantiomers is predominantly present, for example in mixtures with an enantiomeric excess (ee) of the L-enantiomer in the range of from 0.1 to 85%. Preferred are racemic mixtures and mixtures of enantiomers containing predominantly the respective L-isomer with an enantiomeric excess (ee) in the range of from 0.1 to 85%, even more preferred from 2.5% to 50%.

Most preferred is the racemic mixture.

The enantiomeric excess can be determined by measuring the polarization (polarimetry) or preferably by chromatography, for example by HPLC with a chiral column, for example with one or more cyclodextrins as immobilized phase. Preferred is determination of the ee by HPLC with an immobilized optically active ammonium salt such as D-penicillamine.

In one embodiment of the present invention, inventive salts may contain in the range of from 0.1 to 5% by weight of one or more optically inactive impurities, at least one of the impurities being at least one of the impurities being selected from iminodiacetic acid, formic acid, glycolic acid, propionic acid, acetic acid and their respective alkali metal salts.

Another impurity of inventive salts is alkali metal hydroxide, for example up to 6% by weight, which is co-precipitated during step (b) of the inventive process.

In one aspect of the present invention, inventive salts may contain less than 0.15% by weight of nitrilotriacetic acid (NTA), preferably 0.01 to 0.08% by weight.

In one aspect of the present invention, inventive salts may contain minor amounts of cations other than alkali metal. It is thus possible that minor amounts, such as 0.001 to 0.5 mol-% of total chelating agent in said inventive salt, based on anion, bear alkali earth metal cations such as $Mg^{2+}$ or $Ca^{2+}$, or transition metal ions such as $Fe^{2+}$ or $Fe^{3+}$ cations.

Inventive salts show excellent properties, especially when used as sequestrant in cleaners for hard surfaces such as, but not limited to automatic dishwashing detergents, and in laundry detergents. Inventive salts have low hygroscopicity and a low tendency to yellowing even in the presence of peroxides, percarbonates and/or perborates.

Another aspect of the present invention relates to the use of inventive salts, and another aspect of the present invention relates to methods of use of the inventive salts. The preferred use of inventive salts is for the manufacture of solid laundry detergent compositions and of solid detergent compositions for hard surface cleaning. Solid laundry detergent compositions and solid detergent compositions for hard surface cleaning may contain some residual moisture, for example 0.1 to 10% by weight, but are otherwise solid mixtures. The residual moisture content may be determined, e.g., under vacuum at 80° C. Another aspect of the present invention relates to solid laundry detergent compositions and to solid detergent compositions for hard surface cleaning.

In the context of the present invention, the term "detergent composition for cleaners" includes cleaners for home care and for industrial or institutional applications. The term "detergent composition for hard surface cleaners" includes compositions for dishwashing, especially hand dishwash and automatic dishwashing and ware-washing, and compositions for other hard surface cleaning such as, but not limited to compositions for bathroom cleaning, kitchen cleaning, floor cleaning, descaling of pipes, window cleaning, car cleaning including truck cleaning, furthermore, open plant cleaning, cleaning-in-place, metal cleaning, disinfectant cleaning, farm cleaning, high pressure cleaning, but not laundry detergent compositions.

In the context of the present invention and unless expressly stated otherwise, percentages in the context of ingredients of laundry detergent compositions are percentages by weight and refer to the total solids content of the respective laundry detergent composition. In the context of the present invention and unless expressly stated otherwise, percentages in the context of ingredients of detergent composition for hard surface cleaning are percentages by weight and refer to the total solids content of the detergent composition for hard surface cleaner.

In one embodiment of the present invention, solid laundry detergent compositions according to the present invention may contain in the range of from 1 to 30% by weight of inventive salt. Percentages refer to the total solids content of the respective laundry detergent composition.

In one embodiment of the present invention, inventive solid detergent compositions for hard surface cleaning may contain in the range of from 1 to 50% by weight of inventive salt, preferably 5 to 40% by weight and even more preferably 10 to 25% by weight. Percentages refer to the total solids content of the respective detergent composition for hard surface cleaning.

Particularly advantageous inventive solid detergent compositions for hard surface cleaning and inventive solid laundry detergent compositions, especially for home care, may contain one or more complexing agent other than inventive salt. Inventive solid detergent compositions for hard surface cleaning and inventive solid laundry detergent compositions may contain one or more complexing agent (in the context of the present invention also referred to as sequestrant) other than a salt according to the present invention. Examples for sequestrants other than a salt according to the present invention are IDS (iminodisuccinate), citrate, phosphonic acid derivatives, for example the disodium salt of hydroxyethane-1,1-diphosphonic acid ("HEDP"), and polymers with complexing groups like, for example, polyethyleneimine in which 20 to 90 mole-% of the N-atoms bear at least one $CH_2COO^-$ group, and their respective alkali metal salts, especially their sodium salts, for example $GLDA\text{-}Na_4$, $IDS\text{-}Na_4$, and trisodium citrate, and phosphates such as STPP (sodium tripolyphosphate). Due to the fact that phosphates raise environmental concerns, it is preferred that advantageous detergent compositions for cleaners and advantageous laundry detergent compositions are free from phosphate. "Free from phosphate" should be understood in the context of the present invention, as meaning that the content of phosphate and polyphosphate is in sum in the range from 10 ppm to 0.2% by weight, determined by gravimetry.

Preferred inventive solid detergent compositions for hard surface cleaning and preferred inventive solid laundry detergent compositions may contain one or more surfactant, preferably one or more non-ionic surfactant.

Preferred non-ionic surfactants are alkoxylated alcohols, di- and multiblock copolymers of ethylene oxide and propylene oxide and reaction products of sorbitan with ethylene oxide or propylene oxide, alkyl polyglycosides (APG), hydroxyalkyl mixed ethers and amine oxides.

Preferred examples of alkoxylated alcohols and alkoxylated fatty alcohols are, for example, compounds of the general formula (III)

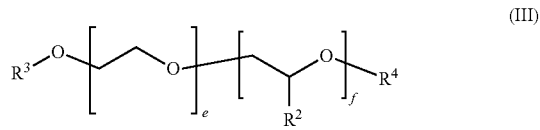

(III)

in which the variables are defined as follows:
$R^2$ is identical or different and selected from hydrogen and linear $C_1\text{-}C_{10}$-alkyl, preferably in each case identical and ethyl and particularly preferably hydrogen or methyl,
$R^3$ is selected from $C_8\text{-}C_{22}$-alkyl, branched or linear, for example n-$C_8H_{17}$, n-$C_{10}H_{21}$, n-$C_{12}H_{25}$, n-$C_{14}H_{29}$, n-$C_{16}H_{33}$ or n-$C_{18}H_{37}$,
$R^4$ is selected from $C_1\text{-}C_{10}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl or isodecyl,
m and n are in the range from zero to 300, where the sum of n and m is at least one, preferably in the range of from 3 to 50. Preferably, m is in the range from 1 to 100 and n is in the range from 0 to 30.

In one embodiment, compounds of the general formula (III) may be block copolymers or random copolymers, preference being given to block copolymers.

Other preferred examples of alkoxylated alcohols are, for example, compounds of the general formula (IV)

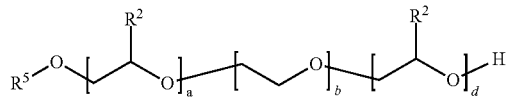
(IV)

in which the variables are defined as follows:

$R^2$ is identical or different and selected from hydrogen and linear $C_1$-$C_{10}$-alkyl, preferably identical in each case and ethyl and particularly preferably hydrogen or methyl, $R^5$ is selected from $C_6$-$C_{20}$-alkyl, branched or linear, in particular n-$C_8H_{17}$, n-$C_{10}H_{21}$, n-$C_{12}H_{25}$, n-$C_{13}H_{27}$, n-$C_{16}H_{31}$, n-$C_{14}H_{29}$, n-$C_{16}H_{33}$, n-$C_{18}H_{37}$, a is a number in the range from zero to 10, preferably from 1 to 6, b is a number in the range from 1 to 80, preferably from 4 to 20, d is a number in the range from zero to 50, preferably 4 to 25.

The sum a+b+d is preferably in the range of from 5 to 100, even more preferably in the range of from 9 to 50.

Preferred examples for hydroxyalkyl mixed ethers are compounds of the general formula (V)

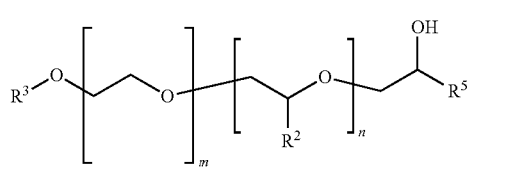
(V)

in which the variables are defined as follows:

$R^2$ is identical or different and selected from hydrogen and linear $C_1$-$C_{10}$-alkyl, preferably in each case identical and ethyl and particularly preferably hydrogen or methyl, $R^3$ is selected from $C_8$-$C_{22}$-alkyl, branched or linear, for example iso-$C_{11}H_{23}$, iso-$C_{13}H_{27}$, n-$C_8H_{17}$, n-$C_{12}H_{25}$, n-$C_{14}H_{29}$, n-$C_{16}H_{33}$ or n-$C_{18}H_{37}$, $R^5$ is selected from $C_6$-$C_{20}$-alkyl, for example n-hexyl, isohexyl, sec-hexyl, n-heptyl, n-octyl, 2-ethylhexyl, n-nonyl, n-decyl, isodecyl, n-dodecyl, n-tetradecyl, n-hexadecyl, and n-octadecyl.

The variables m and n are in the range from zero to 300, where the sum of n and m is at least one, preferably in the range of from 5 to 50. Preferably, m is in the range from 1 to 100 and n is in the range from 0 to 30.

Compounds of the general formula (IV) and (V) may be block copolymers or random copolymers, preference being given to block copolymers.

Further suitable nonionic surfactants are selected from di- and multiblock copolymers, composed of ethylene oxide and propylene oxide. Further suitable nonionic surfactants are selected from ethoxylated or propoxylated sorbitan esters. Amine oxides or alkyl polyglycosides, especially linear $C_4$-$C_{16}$-alkyl polyglucosides and branched $C_8$-$C_{14}$-alkyl polyglucosides such as compounds of general average formula (VI) are likewise suitable.

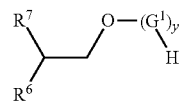
(VI)

wherein:

$R^6$ is $C_1$-$C_4$-alkyl, in particular ethyl, n-propyl or isopropyl, $R^7$ is —$(CH_2)_2$—$R^6$, $G^1$ is selected from monosaccharides with 4 to 6 carbon atoms, especially from glucose and xylose, y in the range of from 1.1 to 4, y being an average number, Further examples of non-ionic surfactants are compounds of general formula (VII) and (VIII)

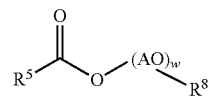
(VII)

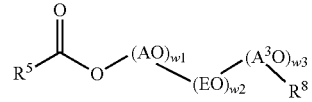
(VIII)

AO is selected from ethylene oxide, propylene oxide and butylene oxide,

EO is ethylene oxide, $CH_2CH_2$—O, $R^8$ selected from $C_8$-$C_{18}$-alkyl, branched or linear, and $R^5$ is defined as above.

$A^3O$ is selected from propylene oxide and butylene oxide, w is a number in the range of from 15 to 70, preferably 30 to 50, w1 and w3 are numbers in the range of from 1 to 5, and w2 is a number in the range of from 13 to 35.

An overview of suitable further nonionic surfactants can be found in EP-A 0 851 023 and in DE-A 198 19 187.

Mixtures of two or more different nonionic surfactants selected from the foregoing may also be present.

Other surfactants that may be present are selected from amphoteric (zwitterionic) surfactants and anionic surfactants and mixtures thereof.

Examples of amphoteric surfactants are those that bear a positive and a negative charge in the same molecule under use conditions. Preferred examples of amphoteric surfactants are so-called betaine-surfactants. Many examples of betaine-surfactants bear one quaternized nitrogen atom and one carboxylic acid group per molecule. A particularly preferred example of amphoteric surfactants is cocamidopropyl betaine (lauramidopropyl betaine).

Examples of amine oxide surfactants are compounds of the general formula (IX)

$$R^9R^{10}R^{11}N \rightarrow O \quad \text{(IX)}$$

wherein $R^9$, $R^{10}$, and $R^{11}$ are selected independently from each other from aliphatic, cycloaliphatic or $C_2$-$C_4$-alkylene $C_{10}$-$C_{20}$-alkylamido moieties. Preferably, $R^9$ is selected from $C_8$-$C_{20}$-alkyl or $C_2$-$C_4$-alkylene $C_{10}$-$C_{20}$-alkylamido and $R^{10}$ and $R^{11}$ are both methyl.

A particularly preferred example is lauryl dimethyl aminoxide, sometimes also called lauramine oxide. A further particularly preferred example is cocamidylpropyl dimethylaminoxide, sometimes also called cocamidopropylamine oxide.

Examples of suitable anionic surfactants are alkali metal and ammonium salts of $C_8$-$C_{18}$-alkyl sulfates, of $C_8$-$C_{18}$-fatty alcohol polyether sulfates, of sulfuric acid half-esters of ethoxylated $C_4$-$C_{12}$-alkylphenols (ethoxylation: 1 to 50 mol of ethylene oxide/mol), $C_{12}$-$C_{18}$ sulfo fatty acid alkyl esters, for example of $C_{12}$-$C_{18}$ sulfo fatty acid methyl esters, furthermore of $C_{12}$-$C_{18}$-alkylsulfonic acids and of $C_{10}$-$C_{18}$-alkylarylsulfonic acids. Preference is given to the alkali metal salts of the aforementioned compounds, particularly preferably the sodium salts.

Further examples for suitable anionic surfactants are soaps, for example the sodium or potassium salts of stearic acid, oleic acid, palmitic acid, ether carboxylates, and alkylether phosphates.

Preferably, inventive laundry detergent compositions contain at least one anionic surfactant.

In one embodiment of the present invention, inventive solid laundry detergent compositions may contain 0.1 to 60% by weight of at least one surfactant, selected from anionic surfactants, amphoteric surfactants and amine oxide surfactants.

In one embodiment of the present invention, inventive solid detergent compositions for cleaners may contain 0.1 to 60% by weight of at least one surfactant, selected from anionic surfactants, amphoteric surfactants and amine oxide surfactants.

In a preferred embodiment, inventive solid detergent compositions for cleaners and especially those for automatic dishwashing do not contain any anionic surfactant.

Inventive solid detergent compositions for hard surface cleaning and inventive solid laundry detergent compositions may contain at least one bleaching agent, also referred to as bleach. Bleaching agents may be selected from chlorine bleach and peroxide bleach, and peroxide bleach may be selected from inorganic peroxide bleach and organic peroxide bleach. Preferred are inorganic peroxide bleaches, selected from alkali metal percarbonate, alkali metal perborate and alkali metal persulfate.

Examples of organic peroxide bleaches are organic percarboxylic acids, especially organic percarboxylic acids.

In inventive solid detergent compositions for hard surface cleaning and in inventive solid laundry detergent compositions, alkali metal percarbonates, especially sodium percarbonates, are preferably used in coated form. Such coatings may be of organic or inorganic nature. Examples are glycerol, sodium sulfate, silicate, sodium carbonate, and combinations of at least two of the foregoing, for example combinations of sodium carbonate and sodium sulfate.

Suitable chlorine-containing bleaches are, for example, 1,3-dichloro-5,5-dimethylhydantoin, N-chlorosulfamide, chloramine T, chloramine B, sodium hypochlorite, calcium hypochlorite, magnesium hypochlorite, potassium hypochlorite, potassium dichloroisocyanurate and sodium dichloroisocyanurate.

Inventive solid detergent compositions for hard surface cleaning and inventive solid laundry detergent compositions may comprise, for example, in the range from 3 to 10% by weight of chlorine-containing bleach.

Inventive solid detergent compositions for hard surface cleaning and inventive solid laundry detergent compositions may comprise one or more bleach catalysts. Bleach catalysts can be selected from bleach-boosting transition metal salts or transition metal complexes such as, for example, manganese-, iron-, cobalt-, ruthenium- or molybdenum-salen complexes or carbonyl complexes. Manganese, iron, cobalt, ruthenium, molybdenum, titanium, vanadium and copper complexes with nitrogen-containing tripod ligands and also cobalt-, iron-, copper- and ruthenium-amine complexes can also be used as bleach catalysts.

Inventive solid detergent compositions for hard surface cleaning and inventive solid laundry detergent compositions may comprise one or more bleach activators, for example N-methylmorpholinium-acetonitrile salts ("MMA salts"), trimethylammonium acetonitrile salts, N-acylimides such as, for example, N-nonanoylsuccinimide, 1,5-diacetyl-2,2-dioxohexahydro-1,3,5-triazine ("DADHT") or nitrile quats (trimethylammonium acetonitrile salts).

Further examples of suitable bleach activators are tetraacetylethylenediamine (TAED) and tetraacetylhexylenediamine.

Inventive solid detergent compositions for hard surface cleaning and inventive solid laundry detergent compositions may comprise one or more corrosion inhibitors. In the present case, this is to be understood as including those compounds which inhibit the corrosion of metal. Examples of suitable corrosion inhibitors are triazoles, in particular benzotriazoles, bisbenzotriazoles, aminotriazoles, alkylaminotriazoles, also phenol derivatives such as, for example, hydroquinone, pyrocatechol, hydroxyhydroquinone, gallic acid, phloroglucinol or pyrogallol.

In one embodiment of the present invention, inventive solid detergent compositions for hard surface cleaning and inventive solid laundry detergent compositions comprise in total in the range from 0.1 to 1.5% by weight of corrosion inhibitor.

Inventive solid detergent compositions for hard surface cleaning and inventive solid laundry detergent compositions may comprise one or more builders, selected from organic and inorganic builders. Examples of suitable inorganic builders are sodium sulfate or sodium carbonate or silicates, in particular sodium disilicate and sodium metasilicate, zeolites, sheet silicates, in particular those of the formula $\alpha$-$Na_2Si_2O_5$, $\beta$-$Na_2Si_2O_5$, and $\delta$-$Na_2Si_2O_5$, also fatty acid sulfonates, $\alpha$-hydroxypropionic acid, alkali metal malonates, fatty acid sulfonates, alkyl and alkenyl disuccinates, tartaric acid diacetate, tartaric acid monoacetate, oxidized starch, and polymeric builders, for example polycarboxylates and polyaspartic acid.

Examples of organic builders are especially polymers and copolymers. In one embodiment of the present invention, organic builders are selected from polycarboxylates, for example alkali metal salts of (meth)acrylic acid homopolymers or (meth)acrylic acid copolymers.

Suitable comonomers are monoethylenically unsaturated dicarboxylic acids such as maleic acid, fumaric acid, maleic anhydride, itaconic acid and citraconic acid. A suitable polymer is in particular polyacrylic acid, which preferably has an average molecular weight $M_w$ in the range from 2000 to 40 000 g/mol, preferably 2000 to 10 000 g/mol, in particular 3000 to 8000 g/mol. Also of suitability are copolymeric polycarboxylates, in particular those of acrylic acid with methacrylic acid and of acrylic acid or methacrylic acid with maleic acid and/or fumaric acid, and in the same range of molecular weight.

It is also possible to use copolymers of at least one monomer from the group consisting of monoethylenically unsaturated $C_3$-$C_{10}$-mono- or $C_4$-$C_{10}$-dicarboxylic acids or anhydrides thereof, such as maleic acid, maleic anhydride, acrylic acid, methacrylic acid, fumaric acid, itaconic acid and citraconic acid, with at least one hydrophilic or hydrophobic monomer as listed below.

Suitable hydrophobic monomers are, for example, isobutene, diisobutene, butene, pentene, hexene and styrene, olefins with 10 or more carbon atoms or mixtures thereof, such as, for example, 1-decene, 1-dodecene, 1-tetradecene, 1-hexadecene, 1-octadecene, 1-eicosene, 1-docosene, 1-tetracosene and 1-hexacosene, $C_{22}$-α-olefin, a mixture of $C_{20}$-$C_{24}$-α-olefins and polyisobutene having on average 12 to 100 carbon atoms per molecule.

Suitable hydrophilic monomers are monomers with sulfonate or phosphonate groups, and also nonionic monomers with hydroxyl function or alkylene oxide groups. By way of example, mention may be made of: allyl alcohol, isoprenol, methoxypolyethylene glycol (meth)acrylate, methoxypolypropylene glycol (meth)acrylate, methoxypolybutylene glycol (meth)acrylate, methoxypoly(propylene oxide-co-ethylene oxide) (meth)acrylate, ethoxypolyethylene glycol (meth)acrylate, ethoxypolypropylene glycol (meth)acrylate, ethoxypolybutylene glycol (meth)acrylate and ethoxypoly(propylene oxide-co-ethylene oxide) (meth)acrylate. Polyalkylene glycols here may comprise 3 to 50, in particular 5 to 40 and especially 10 to 30 alkylene oxide units per molecule.

Particularly preferred sulfonic-acid-group-containing monomers here are 1-acrylamido-1-propanesulfonic acid, 2-acrylamido-2-propanesulfonic acid, 2-acrylamido-2-methylpropanesulfonic acid, 2-methacrylamido-2-methylpropanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)propanesulfonic acid, 2-methyl-2-propene-1-sulfonic acid, styrenesulfonic acid, vinylsulfonic acid, 3-sulfopropyl acrylate, 2-sulfoethyl methacrylate, 3-sulfopropyl methacrylate, sulfomethacrylamide, sulfomethylmethacrylamide, and salts of said acids, such as sodium, potassium or ammonium salts thereof.

Particularly preferred phosphonate-group-containing monomers are vinylphosphonic acid and its salts.

A further example of builders is carboxymethyl inulin.

Moreover, amphoteric polymers can also be used as builders.

Inventive solid detergent compositions for hard surface cleaning and inventive solid laundry detergent compositions may comprise, for example, in the range from in total 10 to 70% by weight, preferably up to 50% by weight, of builder. In the context of the present invention, MGDA is not counted as builder.

In one embodiment of the present invention, inventive solid detergent compositions for hard surface cleaning and inventive solid laundry detergent compositions may comprise one or more cobuilders.

Inventive solid detergent compositions for hard surface cleaning and inventive solid laundry detergent compositions may comprise one or more antifoams, selected for example from silicone oils and paraffin oils.

In one embodiment of the present invention, inventive solid detergent compositions for hard surface cleaning and inventive solid laundry detergent compositions comprise in total in the range from 0.05 to 0.5% by weight of antifoam.

Inventive solid detergent compositions for hard surface cleaning and inventive solid laundry detergent compositions may comprise one or more enzymes. Examples of enzymes are lipases, hydrolases, amylases, proteases, cellulases, esterases, pectinases, lactases and peroxidases.

In one embodiment of the present invention, inventive solid detergent compositions for hard surface cleaning and inventive solid laundry detergent compositions may comprise, for example, up to 5% by weight of enzyme, preference being given to 0.1 to 3% by weight. Said enzyme may be stabilized, for example with the sodium salt of at least one $C_1$-$C_3$-carboxylic acid or $C_4$-$C_{10}$-dicarboxylic acid. Preferred are formates, acetates, adipates, and succinates.

In one embodiment of the present invention, inventive solid detergent compositions for hard surface cleaning and inventive solid laundry detergent compositions comprise at least one zinc salt. Zinc salts can be selected from water-soluble and water-insoluble zinc salts. In this connection, within the context of the present invention, water-insoluble is used to refer to those zinc salts which, in distilled water at 25° C., have a solubility of 0.1 g/l or less. Zinc salts which have a higher solubility in water are accordingly referred to within the context of the present invention as water-soluble zinc salts.

In one embodiment of the present invention, zinc salt is selected from zinc benzoate, zinc gluconate, zinc lactate, zinc formate, $ZnCl_2$, $ZnSO_4$, zinc acetate, zinc citrate, $Zn(NO_3)_2$, $Zn(CH_3SO_3)_2$ and zinc gallate, preferably $ZnCl_2$, $ZnSO_4$, zinc acetate, zinc citrate, $Zn(NO_3)_2$, $Zn(CH_3SO_3)_2$ and zinc gallate.

In another embodiment of the present invention, zinc salt is selected from ZnO, ZnO.aq, $Zn(OH)_2$ and $ZnCO_3$. Preference is given to ZnO.aq.

In one embodiment of the present invention, zinc salt is selected from zinc oxides with an average particle diameter (weight-average) in the range from 10 nm to 100 μm.

The cation in zinc salt can be present in complexed form, for example complexed with ammonia ligands or water ligands, and in particular be present in hydrated form. To simplify the notation, within the context of the present invention, ligands are generally omitted if they are water ligands.

Depending on how the pH of mixture according to the invention is adjusted, zinc salt can change. Thus, it is for example possible to use zinc acetate or $ZnCl_2$ for preparing formulation according to the invention, but this converts at a pH of 8 or 9 in an aqueous environment to ZnO, $Zn(OH)_2$ or ZnO.aq, which can be present in non-complexed or in complexed form.

Zinc salt may be present in those detergent compositions for cleaners according to the invention which are solid at room temperature are preferably present in the form of particles which have for example an average diameter (number-average) in the range from 10 nm to 100 μm, preferably 100 nm to 5 μm, determined for example by X-ray scattering.

Zinc salt may be present in those detergent compositions for home which are liquid at room temperature in dissolved or in solid or in colloidal form.

In one embodiment of the present invention, detergent compositions for cleaners and laundry detergent compositions comprise in total in the range from 0.05 to 0.4% by weight of zinc salt, based in each case on the solids content of the composition in question.

Here, the fraction of zinc salt is given as zinc or zinc ions. From this, it is possible to calculate the counterion fraction.

In one embodiment of the present invention, inventive solid detergent compositions for hard surface cleaning and inventive solid laundry detergent compositions are free from heavy metals apart from zinc compounds. Within the context of the present, this may be understood as meaning that detergent compositions for cleaners and laundry detergent compositions according to the invention are free from those heavy metal compounds which do not act as bleach catalysts, in particular of compounds of iron and of bismuth. Within the context of the present invention, "free from" in connection with heavy metal compounds is to be understood as meaning that the content of heavy metal compounds which do not act as bleach catalysts is in sum in the range from 0 to 100 ppm, determined by the leach method and based on the solids content. Preferably, formulation according to the invention has, apart from zinc, a heavy metal content below 0.05 ppm, based on the solids content of the formulation in question. The fraction of zinc is thus not included.

Within the context of the present invention, "heavy metals" are defined to be any metal with a specific density of at least 6 g/cm$^3$ with the exception of zinc. In particular, the heavy metals are metals such as bismuth, iron, copper, lead, tin, nickel, cadmium and chromium.

Preferably, inventive solid detergent compositions for hard surface cleaning and inventive solid laundry detergent compositions comprise no measurable fractions of bismuth compounds, i.e. for example less than 1 ppm.

In one embodiment of the present invention, inventive solid detergent compositions for hard surface cleaning and inventive solid laundry detergent compositions comprise one or more further ingredient such as fragrances, dyestuffs, organic solvents, buffers, tablet disintegrants, and/or acids such as methylsulfonic acid.

Preferred example detergent compositions for automatic dishwashing may be selected according to Table 1.

TABLE 1

Example detergent compositions for automatic dishwashing

| All amounts in g/sample | ADW.1 | ADW.2 | ADW.3 |
|---|---|---|---|
| inventive salt, racemic MGDA-Na$_3$ | 30 | 22.5 | 15 |
| Protease | 2.5 | 2.5 | 2.5 |
| Amylase | 1 | 1 | 1 |
| n-C$_{18}$H$_{37}$—O(CH$_2$CH$_2$O)$_9$H | 5 | 5 | 5 |
| Polyacrylic acid M$_w$ 4000 g/mol as sodium salt, completely neutralized | 10 | 10 | 10 |
| Sodium percarbonate | 10.5 | 10.5 | 10.5 |
| TAED | 4 | 4 | 4 |
| Na$_2$Si$_2$O$_5$ | 2 | 2 | 2 |
| Na$_2$CO$_3$ | 19.5 | 19.5 | 19.5 |
| Sodium citrate dihydrate | 15 | 22.5 | 30 |
| HEDP | 0.5 | 0.5 | 0.5 |
| ethoxylated polyethylenimine, 20 EO/NH group, M$_n$: 30,000 g/mol | optionally: 0.1 | optionally: 0.1 | optionally: 0.1 |

Laundry detergent compositions according to the invention are useful for laundering any type of laundry, and any type of fibres. Fibres can be of natural or synthetic origin, or they can be mixtures of natural of natural and synthetic fibres. Examples of fibers of natural origin are cotton and wool. Examples for fibers of synthetic origin are polyurethane fibers such as Spandex® or Lycra®, polyester fibers, or polyamide fibers. Fibers may be single fibers or parts of textiles such as knitwear, wovens, or nonwovens.

The invention is further illustrated by working examples.

General Remarks:

Working Examples

The X-ray powder diffractometer measurements were carried out on a D8 Advance® diffractometer from Bruker AXS (Karlsruhe). In reflection with Cu-K α-radiation was measured with a variable diaphragm adjustment on the primary side and on the secondary side. The measurement range was 2° to 80° 2-theta, the step width 0.01° and the measurement time per angle step 3.6 seconds.

With exception of ee values and of degrees of crystallinity, percentages in the context of the examples refer to percent by weight unless expressly indicated otherwise.

Normal pressure: 1013 mbar

I.1 Synthesis of a Solution of a Partially Neutralized L-Alanine Bis-acetonitrile A 5-liter stirred flask was charged with 2,100 g of de-ionized water and heated to 40° C. 1,200 g of L-alanine (13.47 mol, 98% ee) were added. To the resultant slurry 700 g of 50% by weight aqueous sodium hydroxide solution (8.75 mol) were added over a period of 30 minutes. During the addition of sodium hydroxide solution the temperature raised to 60° C. After complete addition of the sodium hydroxide solution the slurry was stirred at 60° for 30 minutes. A clear solution was obtained.

A 5-liter stirred flask was charged with 500 ml of water and heated to 40° C. Then, 2,373 g of L-alanine solution according to step (a.1) (8.00 mole), 1627 g of 30% by weight aqueous formaldehyde solution (16.27 mole) and 220 g of hydrogen cyanide (8.15 mol) were added simultaneously within 60 minutes. Then, additional 220 g of hydrogen cyanide (8.15 mol) were added at 40° C. within 60 minutes. Upon completion of the addition the reaction mixture was stirred for additional 60 minutes at 40° C. A solution was obtained that contained partially neutralized L-alanine bis-acetonitrile.

The resulting aqueous solution, step (a.1), contained 40.00 wt % MGDA-Na$_3$ and 0.08 wt % nitrilotriacetic acid (NTA). The enantiomeric excess of L-MGDA-Na$_3$ (31.6%) was determined by the aforementioned HPLC method.

The resulting aqueous solution, step (a.1), contained 40.00 wt % MGDA-Na$_3$ and 0.08 wt % nitrilotriacetic acid (NTA). The enantiomeric excess of L-MGDA-Na$_3$ (31.6%) was determined by the aforementioned HPLC method.

Step (b.1):

A 0.75-liter jacket stirred vessel made of glass was charged with 918 g of a 40% by weight aqueous (L)-MGDA-Na$_3$ solution (1.35 mole, 31.6% ee, obtained according to (a.1), see above) at room temperature. The resultant solution was heated to 80° C. under stirring. Then, the pressure was lowered. At 300 mbar, 71.1 g water was evaporated within 30 minutes. The reaction mixture was brought to normal pressure and 335 mL of a 50% by weight aqueous sodium hydroxide solution (4.19 mole) were added within 1 hour. The clear solution was seeded with 3.7 g MGDA-Na$_3$ powder (approx. 1% by weight calculated on solid content) and cooled at a rate of 40 K/h to 60° C. After 30 minutes at 60° C., the slurry was cooled with 40 K/h to 40° C. and stirred for 30 minutes. An end-temperature of 20° C. was reached after further cooling using the same rate. The suspension was filtered over a suction filter and the filter cake washed with mother liquid.

The wet filter cake was dried at 90° C. and 0.1 mbar to yield 204 g of white crystalline powder, inventive salt (S.1), containing 86 wt % MGDA-Na$_3$ with 98% crystallinity (modification 1), 12.8% ee and 0.04 wt % NTA.

Step (a.2):

A flask was charged with 608 g (3.04 mol) of 20% by weight sodium hydroxide solution. Within about two hours, an amount of 148 g (1.0 mol) of pure racemic MGDN were introduced at approx. 25° C. Subsequently, the mixture was stirred further under nitrogen first at 30° C. for 3 h and then at 40° C. for 2 h. The mixture was then heated to 170-180° C. in a tubular reactor at approx. 25 bar for 15 minutes. Afterward, the mixture was stripped with nitrogen at 100 to 104° C. within approx. 5 hours. During stripping the solids contents were kept below 45 percent by weight by adding water. This resulted in a yellow-orange solution (Hazen color number: 105) with the following composition:

MGDA-Na$_3$: 257 g (0.95 mol, 95% yield), corresponding to 643 g of a 40 wt % MGDA-Na$_3$ solution, with 0.07 wt % nitrilo-triacetic acid (NTA).

Step (b.2)

A 0.75-liter jacket stirred vessel made of glass was charged with 862.8 g of a 40% by weight aqueous (D,L)-MGDA-Na$_3$ solution (1.27 mole, 0% ee) at room temperature. The resultant solution was heated to 80° C. under stirring. Then, the pressure was lowered. At 340 mbar, 82.2 g water was evaporated within 30 minutes. The reaction mixture was brought to normal pressure and 200 mL of a 50% by weight aqueous sodium hydroxide solution (3.80 mole) were added within 1 hour. The clear solution was seeded with 3.6 g MGDA-Na$_3$ powder (approx. 1% by weight calculated on solid content) and cooled with 30 K/h to 70° C. After 1 hour at 70° C., the slurry was cooled at a rate of 40 K/h to 50° C. and stirred for 30 minutes. An end-temperature of 30° C. was reached after further cooling using the same rate. The slurry was filtered over a suction filter and the filter cake washed with mother liquid.

The wet filter cake was dried at 90° C. and 0.1 mbar to give 255.8 g of white crystalline powder, inventive salt (S.2) containing 84 wt % (D,L)-MGDA-Na$_3$ with 98% crystallinity (modification 1), and 0.04 wt % NTA.

Inventive salts (S.1) and (S.2) showed only very low hygroscopicity. In addition, their stability against percarbonate was excellent.

The invention claimed is:

1. A process for manufacturing a crystalline alkali metal salt of formula (I):

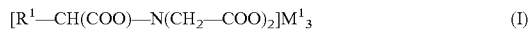
[R$^1$—CH(COO)—N(CH$_2$—COO)$_2$]M$^1$$_3$ (I)

wherein:
each M$^1$ is independently an alkali metal cation selected from the group consisting of sodium and potassium; and
R$^1$ is a C$_1$-C$_4$-alkyl,
the process comprising:
(b) crystallizing said alkali metal salt from an aqueous solution comprising in the range of from 5 to 30% by weight of alkali metal hydroxide, based on the weight of said aqueous solution.

2. The process according to claim 1, wherein said alkali metal salt is racemic or a mixture of enantiomers comprising predominantly the respective L-isomer with an enantiomeric excess (ee) in the range of from 0.1 to 85%.

3. The process according to claim 1, wherein R1 is methyl and all M$^1$ are sodium.

4. The process according to claim 1, wherein (b) comprises providing an aqueous solution of alkali metal salt of formula (I) in an aqueous solution of alkali metal hydroxide, said solution having a temperature of at least 50° C., and cooling down said solution to 35° C. or less at a. cooling rate of 0,1 to 1.5° C./min.

5. The process according to claim 1, wherein said crystallizing comprises cooling crystallization.

6. The process according to claim 1, further comprising (a1):

(a1) saponification of at least one nitrile according to formula (II a) or (II b)

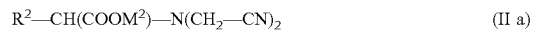
R$^2$—CH(COOM$^2$)—N(CH$_2$—CN)$_2$ (II a)

R$^2$—CH(CN)—N(CH$_2$—CN)$_2$ (II b)

wherein:
R$^2$ is C$_1$-C$_4$-alkyl; and
M$^2$ is an alkali metal or hydrogen,
with an excess of aqueous alkali metal hydroxide solution before subjecting the resultant solution to (b).

7. The process according to claim 1, further comprising (a2) and (a3):

(a2) saponification of at least one nitrile according to formula (II a) or (II b)

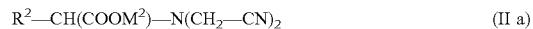
R$^2$—CH(COOM$^2$)—N(CH$_2$—CN)$_2$ (II a)

R$^2$—CH(CN)—N(CH$_2$—CN)$_2$ (II b)

wherein:
R$^2$ is C$_1$-C$_4$-alkyl; and
M$^2$ is an alkali metal or hydrogen,
with a stoichiometric amount of alkali metal hydroxide solution; and
(a3) adding an aqueous alkali metal hydroxide solution before subjecting the resultant solution to (b) or during (b).

8. The process according to claim 1, wherein the aqueous solution that is subjected to (b) is free from ammonia.

9. The process according to claim 6, further comprising:
separating the crystalline alkali metal salt of formula (I) from the aqueous solution, to obtain a mother liquor, wherein the saponification of the nitrile according to formula (II a) or (II b) performed at least partially with the mother liquor.

10. The process according to claim 1, wherein the crystallization is initiated by addition of seed crystals.

11. A solid alkali metal salt of formula (I):

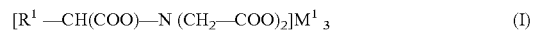
[R$^1$ —CH(COO)—N (CH$_2$—COO)$_2$]M$^1$ $_3$ (I)

wherein:
each M$^1$ is independently an alkali metal cation; and
R$^1$ is a C$_1$-C$_4$-alkyl,
said solid alkali metal salt having a crystallinity in the range of from 90 to 99%, determined by X-ray diffraction.

12. The solid alkali metal salt according to claim 11, wherein said alkali metal salt is racemic or a mixture of enantiomers comprising predominantly the respective L-isomer with an enantiomeric excess (ee) in the range of from 0.1 to 85%.

13. The solid alkali metal salt according to claim 11, wherein said alkali metal salt is a mixture of enantiomers containing predominantly the respective L-isomer with an enantiomeric excess (ee) in the range of from 10 to 35%.

14. The solid alkali metal salt according to claim 11, wherein R$^1$ is methyl and all M$^1$ are sodium.

15. A solid laundry detergent composition comprising the solid alkali metal salt according to claim 11.

* * * * *

UNITED STATES PATENT AND TRADEMARK OFFICE
CERTIFICATE OF CORRECTION

PATENT NO. : 10,421,711 B2
APPLICATION NO. : 16/061007
DATED : September 24, 2019
INVENTOR(S) : Constanze Franzke et al.

It is certified that error appears in the above-identified patent and that said Letters Patent is hereby corrected as shown below:

In the Specification

Column 11, Line 18, "n-$C_{16}H_{31}$," should read -- n-$C_{15}H_{31}$, --;

Column 11, Line 46, after "n-$C_8H_{17}$," insert -- n-$C_{10}H_{21}$, --;

In the Claims

Column 19, Line 54, Claim 4, "0,1" should read -- 0.1 --;

Column 20, Line 33, Claim 9, "(II b) performed" should read -- (II b) is performed --.

Signed and Sealed this
Fifth Day of May, 2020

Andrei Iancu
*Director of the United States Patent and Trademark Office*